United States Patent [19]

Thunberg

[11] Patent Number: 5,446,179
[45] Date of Patent: * Aug. 29, 1995

[54] PROCESS FOR THE PREPARATION OF MICRONUTRIENT BLENDS

[75] Inventor: Jon C. Thunberg, Milford, N.H.

[73] Assignee: Hampshire Chemical Corp., Lexington, Mass.

[ * ] Notice: The portion of the term of this patent subsequent to Oct. 27, 2009 has been disclaimed.

[21] Appl. No.: 136,342

[22] Filed: Oct. 14, 1993

Related U.S. Application Data

[63] Continuation-in-part of Ser. No. 958,376, Oct. 8, 1992, Pat. No. 5,274,151.

[51] Int. Cl.⁶ .............................................. C07F 15/00
[52] U.S. Cl. ........................ 556/148; 252/182.33; 252/182.34; 252/183.13; 423/138; 423/143; 423/179; 71/DIG. 2; 504/190; 504/193
[58] Field of Search ................ 556/148; 423/138, 143, 423/179; 252/182.33, 182.34, 183.13; 71/DIG. 2; 504/190, 193

[56] References Cited

U.S. PATENT DOCUMENTS

| | | | |
|---|---|---|---|
| 2,534,781 | 12/1950 | McMahon | 252/99 |
| 2,816,060 | 12/1957 | Carter | 167/68 |
| 2,859,104 | 11/1958 | Kroll | 71/1 |
| 2,891,854 | 6/1959 | Kroll | 71/1 |
| 2,906,762 | 9/1959 | Knell et al. | 260/439 |
| 2,931,716 | 4/1960 | Kelley | 71/1 |
| 2,943,100 | 6/1960 | Holstein | 260/429 |
| 3,080,410 | 3/1963 | Le Blanc | 260/439 |
| 3,150,160 | 9/1964 | Dexter | 260/439 |
| 3,661,953 | 5/1972 | Carlson | 260/439 R |
| 3,753,675 | 8/1973 | Young | 71/1 |
| 3,903,119 | 9/1975 | Petree et al. | 260/439 R |
| 3,981,712 | 9/1976 | Petree et al. | 71/1 |
| 4,056,381 | 11/1977 | Kenton | 71/36 |
| 4,130,582 | 12/1978 | Petree et al. | 562/448 |
| 4,181,516 | 1/1980 | Gray | 71/25 |
| 5,159,094 | 10/1992 | Thunberg | 556/148 |
| 5,274,151 | 12/1993 | Thunberg | 556/148 |

FOREIGN PATENT DOCUMENTS

| | | |
|---|---|---|
| 197801 | 1/1977 | Germany . |
| 58-021690 | 2/1983 | Japan . |

OTHER PUBLICATIONS

Chemical Abstracts 88:163127c vol. 88, 1978 p. 732.
Kirk Othmer, Encyclopedia of Chemical Technology, 3rd Edition vol. 10 pp. 80–85 (1980).

*Primary Examiner*—José G. Dees
*Assistant Examiner*—Porfirio Nazario-Gonzalez
*Attorney, Agent, or Firm*—Nields & Lemack

[57] ABSTRACT

Metal complexes having high bulk density and a process for the production of the same without the generation of heavy metal-contaminated effluents are disclosed. Solid complexes of EDTANaFe and EDTAKFe having high bulk densities are formed by reaction with mixed metal solutions containing low chromium levels, followed by total drying of the resulting mixture in the same processing equipment without the prior separation of the sulfate salts formed. The amounts of the various metals in any given formulation can be preselected.

16 Claims, No Drawings

PROCESS FOR THE PREPARATION OF MICRONUTRIENT BLENDS

This application is a continuation-in-part of U.S. application Ser. No. 07/958,376 filed Oct. 8, 1992, now U.S. Pat. No. 5,274,151.

BACKGROUND OF THE INVENTION

Conventional processes for the production of solid Fe(III) chelates for agricultural and other uses generate waste crystal liquors with high concentrations of iron and heavy metals, particularly chromium. Such heavy metals are problematic from an environmental standpoint. The economic implications of properly disposing of such streams are significant, and are often prohibitive. In addition, the waste liquor can contain some soluble product. Although disposal of the waste liquors without recovering the product results in yield loss, recovery of contained product is not economical.

A conventional process for producing the complexes involves reacting chelating agents, such as $EDTNa_4$ or $DTPANa_5$, with ferric chloride solution, followed by filtration, washing and drying. However, one major source of chromium contamination is the ferric chloride used as the ferric iron source. Where low cost grade ferric chloride derived from scrap iron is used, the chromium concentration of the waste streams produced is on the order of 30 ppm. Higher grade ferric chloride can be used, which can reduce the chromium concentration in the waste streams to about 2-3 ppm; however, this higher grade ferric chloride is more expensive. A further drawback of ferric chloride is the highly corrosive properties of the slurries and liquors produced from the chelating agent/ferric chloride reactions.

Prior art drying processes include spray drying and drum drying. However, the resulting product is often very dusty, which creates handling problems. Accordingly, there is a need to find an alternative production process which reduces or eliminates the generation of high heavy metal effluents without adding significant cost.

Fertilizer formulations often contain secondary nutrients or micronutrients. These are metals, usually in the form of metal complexes. EDTA is the most commonly used chelating agent and the major micronutrient metals are iron, copper, manganese and zinc. Several other metals are also used as micronutrients in such formulations, including boron, molybdenum and cobalt. Secondary nutrients are calcium and magnesium. The major components of fertilizer formulations are potash, phosphate and nitrogen compounds. To prepare these formulations, the components are blended. This operation requires adding to the blender the major components plus very small amounts of two or more micronutrients or secondary nutrients, each of which must be precisely weighed and thoroughly blended. The blending operation could be simplified and made more efficient if a single mixture of all the micronutrients and secondary nutrients were available as a single blend. One object of this invention is to provide such a blend.

SUMMARY OF THE INVENTION

The problems of the prior art have been solved by the instant invention, which provides solid complexes having high bulk density and a process for the production of the same without the generation of heavy metal-contaminated effluents. In particular, the present invention relates to the production of blends of metal chelates of EDTA and non-complexed metals in any desired ratio, the blends having high bulk densities. Solutions of metal sulfates and other inorganic salts or oxides are reacted with solutions of $EDTANa_4$ or $EDTAK_4$, followed by total drying of the resulting mixture without the prior separation of the sulfate salts formed. The reaction, mixing and drying processes are carried out in the same processing equipment. By eliminating the separation step and drying the total reaction product, no waste liquor is generated, and a uniform blend of micronutrients is produced. The product loss of prior art processes due to the presence of some soluble product in the waste liquor is thereby eliminated.

DETAILED DESCRIPTION OF THE INVENTION

The present invention concerns a total drying process for preparation of blends of metal complexes and the resulting products formed thereby. Preferably, the equipment used is a jacketed vessel which is a combination of a high-torque mixer or reactor and a vacuum dryer, such that the mixing or reaction and the subsequent drying are carried out in the same equipment chamber. Scrapers or ploughshares mounted on the agitator shaft create a mechanically fluidized action to agitate the particles to be dried and to free the heat transfer surface of dried material. In addition, high shear choppers reduce large agglomerate masses to promote thoroughly dried particle interiors. Preferably, the equipment utilizes a hydraulic drive and should be constructed of stainless steel, preferably 316 stainless steel. Such equipment is available from Littleford Bros, Inc., Florence, Ky.

In accordance with the present invention, prior to drying, a solution of metal sulfates and other inorganic salts or oxides in predetermined ratios is produced. To the solution, an equivalent amount of $EDTANa_4$ or $EDTAK_4$ solution is added which has been previously acidified with acid to just neutralize the contained free alkali. The reaction is illustrated for $EDTANa_4$ and ferric, copper, manganese and zinc sulfates as follows:

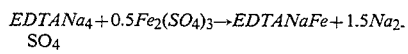

$EDTANa_4 + 0.5Fe_2(SO_4)_3 \rightarrow EDTANaFe + 1.5Na_2SO_4$

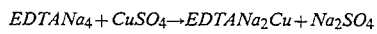

$EDTANa_4 + CuSO_4 \rightarrow EDTANa_2Cu + Na_2SO_4$

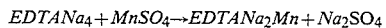

$EDTANa_4 + MnSO_4 \rightarrow EDTANa_2Mn + Na_2SO_4$

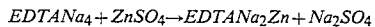

$EDTANa_4 + ZnSO_4 \rightarrow EDTANa_2Zn + Na_2SO_4$

After drying, the product is a uniform blend of $EDTANa_x$ or $EDTAK_x$ metal complexes plus non-complexed metals (such as borate and $MoO_4$) and sodium or potassium sulfate. Exact blends of micronutrients can be produced by preselecting appropriate amounts of reactants and non-reactive metal compounds.

Any metal can be incorporated into the product by using the process disclosed herein. It is not necessary that the metal be complexed with the ligand; the total drying process creates a blend of all of the ingredients that have been incorporated as part of the formulation. Particularly suitable metals include iron, copper, manganese, zinc, boron, molybdenum, magnesium, cobalt, and any other metals suitable as micro or secondary nutrients in fertilizer formulations or that may be desired in the formulation to provide some effect.

An important feature of the present invention is the ability to preselect the ratio of metals depending upon the desired application. For example, possible micronutrient formulations may be comprised of the following micronutrients in the ratios stated:

| Micronutrient | Parts Metal/100 Parts Total Metal |
|---|---|
| FORMULA 1 | |
| Fe | 47.9 |
| Cu | 22.3 |
| Mn | 12.1 |
| Zn | 17.7 |
| FORMULA 2 | |
| Fe | 79.8 |
| Mn | 20.2 |
| FORMULA 3 | |
| Fe | 57.1 |
| Cu | 16.2 |
| Mn | 9.0 |
| Zn | 17.7 |

Upon preselecting the desired ratios of metals in the formulation, the necessary quantity of the source of the metal and the chelating agent (e.g., EDTA) to arrive at that desired amount can be readily ascertained by those skilled in the art.

Other salts of the chelating agents can be used, such as the potassium salts. The pH-adjusted chelating agent is prepared by neutralizing free alkali metal (e.g., sodium or potassium) hydroxide with the acid chelate, or with a mineral acid, such as 50% or 93% sulfuric acid. Suitable chelating agents are available from Hampshire Chemical Corp. as Hamp-ene® 100S or Hamp-ene® K$_4$ 100 and are one of the feedstocks to the reactor/dryer. Other chelating agents can be used as long as the physical properties of the metal complexes thereof do not cause the mix, when it goes through a "mud stage", to become too viscous for the processing equipment. A slurry is then formed by reacting the chelating agent with the solution of metal compounds at about 40°–50° C. Preferably the chelating agent is as concentrated as possible in order to reduce the evaporative load on the drying equipment utilized. In the same piece of equipment, the resulting slurry is vacuum dried to a blend of the alkali metal salts of the metal chelates, alkali metal sulfate, and non-complexed metal compounds such as borate. In contrast to conventional spray drying processes, the instant vacuum drying employs relatively long residence times which depend upon the steam pressure and the vacuum applied.

Since the entire product is vacuum dried without separation of the alkali metal sulfate salt formed, no effluent is produced and the yield is 100% (less any physical losses that occur). Although the metal content of the final product is lower than the prior art products from which the salt has been separated, a significant savings results from the absence of any effluent and the said 100% yield of product.

One surprising aspect of the instant process is the high bulk density of the resulting product formed. A comparison of the total iron content and bulk densities of the products formed in accordance with the instant invention with that of the iron chelate formed from a prior art process (wherein the alkali metal chloride salt (NaCl) has been separated) is illustrated in Table 1:

TABLE 1

| PRODUCT | % Fe | BULK DENSITY LB/Cu Ft |
|---|---|---|
| EDTANaFe (prior art) | 12.6 | 37.1 |
| EDTANaFe/Na$_2$SO$_4$ | 8.73 | 62.1 |
| EDTAKFe/K$_2$SO$_4$ | 7.80 | 61.8 |

The very high bulk densities of the instant products is a further advantage which offsets the slightly lower iron content of the products due to the presence of the alkali metal sulfate.

The total dried product may be milled to remove any gritty material. For commercial applications, it may be desirable to have 100% of the material pass through a 25 mesh sieve. A sieve analysis has demonstrated that about 7% of EDTANaFe/Na$_2$SO$_4$ is greater than 25 mesh and therefore requires milling to meet the desirable specifications.

It would be obvious to those skilled in the art that the disclosed process should be generally applicable to preparation of metal complexes of ligands other than EDTA.

The following examples will serve to illustrate various embodiments of the instant invention. The processes of Examples 1 and 2 were carried out in a small commercial reactor/dryer.

EXAMPLE 1

Production of EDTANaFe/Na$_2$SO$_4$

The equipment used was a Littleford reactor/dryer model MR5. EDTANa$_4$ solution was charged to a hold tank and free alkali therein was neutralized with 93% sulfuric acid. As the iron source, 50% Fe$_2$(SO$_4$)$_3$ was used. The Fe$_2$(SO$_4$)$_3$ was charged to the reactor/dryer and warmed to about 40° C. The neutralized chelate was then added in an amount of 3% excess over iron, and the resulting slurry was vacuumed dried to a blend of EDTANaFe and Na$_2$SO$_4$. The data are provided in Table II.

EXAMPLE 2

Production of EDTAKFe/K$_2$SO$_4$

The reaction and drying were carried out as in Example 1, except that the chelating agent was EDTAK$_4$ solution. The data are provided in Table III.

TABLE II

Preparation of EDTANaFe/Na$_2$SO$_4$ in MR5 Reactor/Dryer at the 1.0 Lb Mole Scale

| | % Active Ingredient | Molecular Weight | Lb Moles | Pounds at 100% A.I. | Pounds at Actual A.I. |
|---|---|---|---|---|---|
| Hamp-ene 100S (EDTANa4) | 38.0% | 380.2 | 1.030 | 392 | 1031 |
| Free NaOH in H-100S | 1.5% | 40.0 | 0.386 | | |
| H2SO4 (to neutralize NaOH) | 93.0% | 98.0 | 0.193 | 19 | 20 |
| Fe2(SO4)3 | 50.0% | 399.9 | 0.500 | 200 | 400 |
| Total | | | | | 1451 |
| PRODUCT | % Fe | | | | |
| EDTANaFe | | 367.1 | 1.000 | 367 | |
| Na2SO4 | | 142.0 | 1.693 | 240 | |

TABLE II-continued

Preparation of EDTANaFe/Na2SO4 in MR5 Reactor/Dryer at the 1.0 Lb Mole Scale

|  | % Active Ingredient | Molecular Weight | Lb Moles | Pounds at 100% A.I. | Actual A.I. |
|---|---|---|---|---|---|
| Total Anhydrous Product | 9.2% |  |  | 608 |  |
| Total Product at 8.7% Fe | 8.7% |  |  | 642 |  |

Note:
the 8.7% Fe value was the Fe content of product produced from the MR5 Reactor/Dryer

TABLE III

Preparation of EDTAKFe/K2SO4 IN MR5 Reactor/Dryer at the 1.0 Lb Mole Scale

|  | % Active Ingredient | Molecular Weight | Lb Moles | Pounds at 100% A.I. | Actual A.I. |
|---|---|---|---|---|---|
| Hamp-ene K4 100S (EDTAK4) | 44.4% | 444.6 | 1.030 | 458 | 1031 |
| Free KOH in H-K4 100S | 1.5% | 56.1 | 0.276 |  |  |
| H2SO4 (to neutralize KOH) | 93.0% | 98.0 | 0.138 | 14 | 15 |
| Fe2(SO4)3 | 50.0% | 399.9 | 0.500 | 200 | 400 |
| Total |  |  |  |  | 1446 |
| PRODUCT | % Fe |  |  |  |  |
| EDTAKFe |  | 383.2 | 1.000 | 383 |  |
| K2SO4 |  | 174.3 | 1.638 | 285 |  |
| Total Anhydrous Product | 8.4% |  |  | 669 |  |
| Total Product at 8.7% Fe | 7.8% |  |  | 716 |  |

Note:
the 7.8% Fe value was the Fe content of product produced from the MR5 Reactor/Dryer

EXAMPLES 3-5

The process used to prepare these samples was designed to simulate the commercial reactor/dryer process equipment.

The free NaOH of EDTANa4 (Hamp-ene ® 100S) was neutralized with sulfuric acid and the Ca chelation value (assay) of this solution was determined. To a stainless steel beaker on a stirring hot plate was charged 50% ferric sulfate, 12% Zn solution (as ZnSO4), dry CuSO4 monohydrate and/or dry MnSO4 monohydrate, the amounts of each depending upon the specific blend of micronutrients in Formulas 1, 2, and 3 above. The raw material formulas are listed below in Table IV. The actual laboratory charges to produce these formulations are set forth in Table V. The mixture of metal compounds was heated to approximately 65° C. or until a clear solution was obtained. This solution was transferred to a 1 liter round bottom vacuum flask which was then mounted on a rotary evaporator and rotated in a 60° C. bath. A slight vacuum was pulled and the neutralized EDTANa4 was added over a period of about 20 minutes. Crystallization occurred when about half of the EDTANa4 had been added. Full vacuum was applied and the mixture was dried to a moist solid. (The vacuum was occasionally interrupted to scrape material off the walls of the flask.) The moist solid was then removed and drying was finished in a 105° C. oven. No tackiness was observed and adhesion to the walls was minimal. All samples dried to a crumbly moist cake, indicating that the products would process well in the commercial reactor/dryer equipment. The dried products were weighed and ground to pass a 20 mesh screen. The 5% pH was measured and found to be 6.56, 6.37 and 6.56 for Formulations 1, 2 and 3, respectively.

TABLE IV

Raw Materials for Preparation of Chelated Mixed Micronutrients for Examples 3-5

| | Molecular Weights | Source of Metal | % Metal or EDTANa4 |
|---|---|---|---|
| Fe | 55.85 | 50% Fe2(SO4)3 | 12.5% |
| Cu | 63.55 | CuSO4.H2O | 35.7% |
| Mn | 54.94 | MnSO4.H2O | 29.5% |
| Zn | 65.38 | ZnSO4 Solution | 12.0% |
| EDTANa4 | 380.18 | H-100S (neutralized) | 37.9% |

TABLE V

Charges for Laboratory Preparations for Examples 3-5

| | Desired Metal Ratio | | Laboratory Preparations | |
|---|---|---|---|---|
| | Weight Ratio | Mole Ratio | Grams of Raw Material Source | Ratioed to Capacity of 1L Flask |
| FORMULA NO. 1 | | | | |
| Fe | 117.5 | 2.104 | 940.8 | 94.9 |
| Cu | 54.7 | 0.861 | 153.2 | 15.5 |
| Mn | 29.7 | 0.541 | 100.7 | 10.2 |
| Zn | 43.3 | 0.662 | 360.8 | 36.4 |
| Total Moles | | 4.168 | | 0.0 |
| H-100S | | 4.376 | 4389.7 | 443.0 |
| Total Grams | | | 5945.1 | 600.0 |
| FORMULA NO. 2 | | | | |
| Fe | 117.5 | 2.104 | 940.8 | 147.5 |
| Mn | 29.7 | 0.541 | 100.7 | 15.8 |
| Total Moles | | 2.645 | | 0.0 |
| H-100S | | 2.777 | 2785.4 | 436.7 |
| Total Grams | | | 3826.9 | 600.0 |
| FORMULA NO. 3 | | | | |
| Fe | 60.5 | 1.083 | 484.4 | 110.4 |
| Cu | 17.2 | 0.271 | 48.2 | 11.0 |
| Mn | 9.5 | 0.173 | 32.2 | 7.3 |
| Zn | 18.8 | 0.288 | 156.7 | 35.7 |
| Total Moles | | 1.814 | | 0.0 |
| H-100S | | 1.905 | 1911.1 | 435.6 |
| Total Grams | | | 2632.6 | 600.0 |

EXAMPLES 6-7

The process used to prepare these samples was designed to more closely simulate the reactor/dryer process equipment than Examples 3-5. The raw materials used for these examples are shown in Table VI. The free alkali in a 38% EDTANa4 solution (sold commercially as Hamp-ene® 100S) and a 54% EDTAK4 solution were neutralized with 98% H2SO4. The amount of acid needed in terms of g 98% H2SO4/g mole of EDTANa4 was 14.8 g/M, and in terms of g 98% H2SO4/g mole of EDTAK4 was 10.6 g/M. The metal salts in the amounts shown in Table VII were charged to a 1 L round bottom vacuum flask in the following order to obtain a clear solution of the metal salts: thirty grams of water plus the borax was mixed until dissolved; the 50% ferric sulfate was added and mixed until the crystals formed nearly all dissolved; the ZnSO4 solution was added; the MgSO4 was added and mixed until dissolved; then the CuSO4, MnSO4 and NaRMoO4 were added in that order with mixing between each addition until dissolved. The flask was mounted on a rotary evaporator and rotated without vacuum in a 65° C. bath until a clear solution was obtained. A slight vacuum was then applied and the neutralized EDTA solution was sucked into the flask via an addition tube over ~1 hour. Full vacuum was then applied and the bath temperature was raised to >90° C. Each was stripped to a paste, and the paste was quantitatively transferred to a tared glass tray and placed in an oven. Each product was dried to constant weight at 105° C. The product was weighed and then ground to pass a 20 mesh screen. The calculated compositions of the dry product are shown in Table VIII. The sodium salt had a 1% solution pH of 9.13, a density of 1.153 g/cc (72.0 lb/ft$^3$) and was a greyish powder. The potassium salt had a 1% solution pH of 7.18, a density of 1.279 g/cc (79.8 lb/ft$^3$) and was a greenish powder.

TABLE VI

Raw Materials for Preparation of Chelated Mixed Micronutrients for Examples 6 & 7

| | Molecular Weights | Source of Metal or Ligand | % Metal or EDTAM4 |
|---|---|---|---|
| Fe | 55.85 | 50% Fe2(SO4)3 Solution | 12.5% |
| Cu | 63.55 | CuSO4.H2O | 35.7% |
| Mn | 54.94 | MnSO4.H2O | 29.5% |
| Zn | 65.38 | ZnSO4 Solution | 12.0% |
| B | 10.81 | Na2B4O7.10H2O | 11.3% |
| Mo | 95.94 | Na2MoO4.2H2O | 39.6% |
| Mg | 24.31 | MgSO4 (anhydrous) | 20.2% |
| EDTANa4 | 380.18 | Hamp-ene 100S Neut. | 37.9% |
| EDTAK4 | 444.61 | Hamp-ene K4 100 Neut. | 53.6% |

TABLE VII

Formulas for Laboratory Preparations for Examples 6 & 7

| Metal or Ligand | Weight Ratios | × 100 | Moles | Grams of Raw Material | Charges Actually Used For Total Charge of 600 g | | | |
|---|---|---|---|---|---|---|---|---|
| | | | | | for Na Salt | | for K Salt | |
| | | | | | Moles | Grams | Moles | Grams |
| Fe | 0.15 | 15.0 | 0.269 | 120.0 | 0.126 | 56.21 | 0.146 | 65.29 |
| Cu | 0.07 | 7.0 | 0.110 | 19.6 | 0.052 | 9.18 | 0.060 | 10.67 |
| Mn | 0.05 | 5.0 | 0.091 | 16.9 | 0.043 | 7.94 | 0.050 | 9.22 |
| Zn | 0.06 | 6.0 | 0.092 | 50.0 | 0.043 | 23.42 | 0.050 | 27.20 |
| B | 0.02 | 2.0 | 0.185 | 17.6 | 0.087 | 8.26 | 0.101 | 9.60 |
| Mo | 0.0005 | 0.05 | 0.0005 | 0.13 | 0.00024 | 0.059 | 0.00028 | 0.07 |
| Mg | 0.06 | 6.0 | 0.247 | 29.7 | 0.116 | 13.91 | 0.134 | 16.16 |
| Total moles of metal = | | | 0.994 | | 0.466 | | 0.541 | |
| Total grams of metal salts = | | | | 254.0 | | | | |
| EDTANa4 | | | 1.024 | 1026.9 | 0.480 | 481.01 | | |
| EDTAK4 | | | 1.024 | 848.8 | | | 0.557 | 461.8 |
| Total grams to produce Na Salts = | | | | 1280.9 | | 600.00 | | |
| Total grams to produce K salts = | | | | 1102.8 | | | | 600.0 |

TABLE VIII

Calculated Compositions of Dry Products of Examples 6 & 7 and Properties of the Dry Products

| | Sodium Salt | Potassium Salt |
|---|---|---|
| Estimation of Sulfate Content | | |
| | Moles of Sulfate | |
| From H2SO4 | 0.071 | 0.059 |
| From Fe2(SO4)3 | 1.189 | 0.219 |
| From CuSO4 | 0.052 | 0.060 |
| From MnSO4 | 0.043 | 0.050 |
| From ZnSO4 | 0.043 | 0.050 |
| From MgSO4 | 0.116 | 0.134 |
| Total | 0.513 | 0.572 |
| Calculated Grams of Contained Sulfate | | |
| | Na2SO4 | K2SO4 |
| | 72.80 | 99.66 |
| Calculated Grams of Contained Metal | | |
| Fe | 7.026 | 8.161 |
| Cu | 3.279 | 3.808 |
| Mn | 2.342 | 2.720 |
| Zn | 2.811 | 3.264 |
| B | 0.937 | 1.088 |
| Mo | 0.023 | 0.027 |
| Mg | 2.811 | 3.264 |
| Estimated EDTA Content | | |
| Moles | 0.480 | 0.557 |
| gEDTAH2Na2 | 160.3 | |
| gEDTAH2K2 | | 204.1 |
| Total Calculated Grams = | 252.3 | 326.1 |
| Calculated Composition of Dry Products | | |
| | Composition Wt. % | |
| Na2SO4 | 28.86% | |
| K2SO4 | | 30.57% |
| Fe | 2.79% | 2.50% |
| Cu | 1.30% | 1.17% |
| Mn | 0.93% | 0.83% |
| Zn | 1.11% | 1.00% |
| B | 0.37% | 0.33% |
| Mo | 0.01% | 0.01% |
| Mg | 1.11% | 1.00% |
| *EDTAH2Na2 | 63.52% | |
| *EDTAH2K2 | | 62.59% |
| Total | 100.00% | 100.00% |
| *Free + complexed | | |

| Measured Properties of Dry Products | | |
|---|---|---|
| | Na Salt | K Salt |
| pH of 1% Solution | 9.13 | 7.18 |
| Density, g/cc | 1.153 | 1.279 |
| Density, lb/cu. ft | 72.0 | 79.8 |
| Appearance of powder | grey | greenish |

What is claimed is:

1. A process for producing metal complexes of alkali metal salts of EDTA, comprising:
   a. neutralizing free alkali in an alkali metal salt solution of EDTA with acid;
   b. reacting the neutralized alkali metal salt solution with a solution of metals to form a slurry containing alkali metal sulfate;
   c. vacuum drying said slurry without the prior separation of said alkali metal sulfate, said reacting and vacuum drying steps being carried out in the same processing equipment.

2. The process of claim 1 wherein the alkali metal salt of EDTA is $EDTANa_4$.

3. The process of claim 1 wherein the alkali metal salt of EDTA is $EDTAK_4$.

4. The process of claim 1 wherein the neutralization is carried out with EDTA acid.

5. The process of claim 1 wherein the neutralization is carried out with sulfuric acid.

6. The process of claim 1 wherein the metals in said solution of metals are selected from the group consisting of alkaline earth metals, transition metals, and a combination of alkaline earth and transition metals, and wherein the source of said metals is their sulfate salts.

7. The process of claim 1 wherein the metals in said solution of metals is selected from the group consisting of alkaline earth metals, the source of which is their sulfate salts; transition metals the source of which is their sulfate salts; boron, the source of which is its oxide; and molybdenum, the source of which is its oxide.

8. A process for preparing a micronutrient formulation, comprising:
   a. preselecting the identity and relative amounts of metals desired in said formulation;
   b. preparing a solution of compounds of said preselected metals;
   c. neutralizing free alkali in an alkali metal salt solution of EDTA with acid;
   d. reacting the neutralized alkali metal salt solution with said preselected metal solution to form a slurry containing alkali metal sulfate;
   e. vacuum drying said slurry without the prior separation of said alkali metal sulfate, said reacting and vacuum drying steps being carried out in the same processing equipment.

9. A dry solid composition consisting essentially of blends of alkali metal salts of transition metal EDTA complexes and alkali metal sulfate.

10. The dry solid composition of claim 9, further comprising oxides of boron.

11. The dry solid composition of claim 9, further comprising oxides of molybdenum.

12. The dry solid composition of claim 10, further comprising oxides of molybdenum.

13. The dry solid composition of claim 9, further comprising alkali metal salts of alkaline earth metal complexes of EDTA.

14. The dry solid composition of claim 10, further comprising alkali metal salts of alkaline earth metal complexes of EDTA.

15. The dry solid composition of claim 11, further comprising alkali metal salts of alkaline earth metal complexes of EDTA.

16. The dry solid composition of claim 12, further comprising alkali metal salts of alkaline earth metal complexes of EDTA.

* * * * *